(12) United States Patent
Gerrish

(10) Patent No.: US 6,221,419 B1
(45) Date of Patent: Apr. 24, 2001

(54) PECTIN FOR STABILIZING PROTEINS

(75) Inventor: Timothy C. Gerrish, Kennett Square, PA (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/192,618

(22) Filed: Nov. 5, 1998

(51) Int. Cl.$^7$ ............................ C08B 37/06; A23C 9/154; A23L 1/0524

(52) U.S. Cl. ............................ 426/577; 426/50; 426/583; 426/599; 426/580; 536/2

(58) Field of Search ........................ 426/50, 52, 580, 426/583, 577, 590, 599; 536/2

(56) References Cited

U.S. PATENT DOCUMENTS

| | | |
|---|---|---|
| 4,529,613 | 7/1985 | Mezzino et al. . |
| 5,286,511 | 2/1994 | Klavons et al. . |
| 5,648,112 | 7/1997 | Yang et al. . |
| 5,707,847 | 1/1998 | Christgau et al. . |
| 5,866,190 | 2/1999 | Barey . |

FOREIGN PATENT DOCUMENTS

| | | |
|---|---|---|
| 0 664 300 | * 7/1995 | (EP) . |
| 0 709 033 | * 1/1996 | (EP) . |
| 1474990 | 5/1977 | (GB) . |
| 89/12648 | 12/1989 | (WO) . |
| 91/15517 | 10/1991 | (WO) . |
| 94/25575 | 11/1994 | (WO) . |
| 97/03574 | 2/1997 | (WO) . |

OTHER PUBLICATIONS

Powell et al., *J. Mol. Biol.*, 155(4):517–531, 1982.*
Glahn et al. *Food Ingredients Europe: Conf. Proceed.*, pp. 252–256, Oct. 1994.*
Glahn, Prog. Fd. Nutr. Sci., vol. 6, pp. 171–177, 1982, "Hydrocolloid Stabilization of Protein Suspensions at Low pH".
Speiser et al., Journal of the American Chemical Society, vol. 68 Feb. 1946, pp. 117–133, "Effect of Molecular Association and Charge Distribution of the Gelation of Pectin".
Speiser et al., "Effect of Molecular Weight and Method of Deesterification of the Gelling Behavior of Pectins", 1946, pp. 287–293, J. Am Chem. Soc.
Kohn et al, Die Nahrung, vol. 29, (1985)1, pp. 75–85.
Markovic et al., Experientia (Basel)40(8), 1984, pp. 842–843.
Industrial Gums—Polysaccharides and Their Derivatives, Third Edition, Ed. by Whistler et al, Academic Press, New York, 1993, Chapter 10, pp. 257–291.
Matsuura et al., Agric. Biol. Chem., 51(6), 1675–1677, 1987, "Limit to the Deesterification of Citrus Pectin by Citrus Pectinesterase".
Hill et la., Food Technology, vol. 3, Mar. 1949, pp. 90–93, "Enzyme–Demethylated Pectinates and Their Gelation".
English Abstract of JP 7–264977, 1993.
English Abstract of JP 8–112059, 1994.
Kravtchenko et al., Food Macromolecules and colloids; proceedings of a conference, Dijon, Mar. 1994, 349–355, "Colloidal Stability and Sedimentation of Pectin–Stabilized Acid Milk Drinks".
Kravtchenko et al., "Characterization of Industrial High Methoxy Pectins", pp. 27–35, (date N.A.).
Rolin, Calcium Sensitivity of High Ester Citrus Pectins, pp. 413–422, (date N.A.).
Parker et al., Effect of the Addition of High Methoxy Pectin on the Rheology and Colloidal Stability of Acid Milk Drinks, pp. 307–312, Food Hydrocolloids, 1994.
Glahn, FIA–Japan, PEG/JK (dai–24a)—Apr. 4, 1995, pp. 1–6, Fig. 1 and pp. 1–4, and pp. 1–4, and pp. 1–3.
Glahn et al., Gums and Stabilisers for the Food Industry 8, edited by Phillips et all,, IIRL Press, "Properties and Food Uses of Pectin Fractions", pp. 393–402, (date NA).
Jarvis, Plant, Cell and Environment (1984) 7, 153–164, "Structure and Properties of Pectin Gels in Plant Cell Walls".
Solms et al., Helv. Chim. Acta, 38, pp. 321–329, "Uber den Mechanismus der enzymatischen Verseifung von Pektinstoffen", (date NA).
Kohn et al., Collect. Checz. Chem Commun., 33, pp. 264–269, Distribution of Free Carboxyl Groups in the Pectin Molecule After Treatment With Pectin Esterase, (date NA).
Kravtchenko et al., Di Nahrung, 26, 217–227, 1982.

* cited by examiner

*Primary Examiner*—Keith Hendricks
(74) *Attorney, Agent, or Firm*—Greenblum & Bernstein, P.L.C.

(57) ABSTRACT

Provided is a pectin having (i) a degree of esterification (DE) of 60 to 95%, (ii) a calcium sensitivity ($\Delta$CS) of less than 25 cP, and (iii) a calcium sensitive pectin weight ratio (CSPR) of calcium sensitive pectin (CSP) to the sum of CSP and non-calcium sensitive pectin (NCSP) of 0.7 or more. Such pectin is useful as a stabilizing component of an aqueous acidic beverage, such as a drinking yogurt, which contains a suspension of protein particles formed from, e.g., casein. The pectin can be prepared by treating a substantially non-calcium sensitive pectin having a CSPR of 0.1 or less and a $\Delta$CS of 0–3 with a pectin deesterifying enzyme.

146 Claims, No Drawings

PECTIN FOR STABILIZING PROTEINS

The present invention relates to a pectin for stabilising proteins particularly for use in stabilising proteins present in aqueous acidic beverages. The invention further provides stabilised acidic beverages as well as a process for preparing the pectin.

BACKGROUND OF THE INVENTION

Acidified milk drinks are becoming increasingly popular amongst consumers. Such drinks have long been commercially successful in Japan and parts of south east Asia and are now being introduced into western markets. Such drinks may be yoghurt-based (in which case they are often called drinking yoghurts), Lactobacillus drinks or soft drinks based upon milks These drinks differ from each other for instance in their respective contents of milk solids non-fat (MSNF). MSNF is principally casein. Yoghurt drinks typically contain a minimum of 8% by weight of MSNF, Lactobacillus drinks contain a minimum of 3% by weight of MSNF, whereas soft drinks contain less than 3% by weight of MSNF.

Drinking yoghurts are either distributed fresh and promoted for their content of live lactobacilli, or heat treated prior to distribution to obtain extended shelf life. Heat treated yoghurt drinks must be stabilised to prevent sedimentation of casein particles as such sedimentation leads to the drinks developing an undesirable sandy mouth feel. Even low viscosity MSNF fresh acidified milk drinks have to be stabilised to prevent precipitation of casein particles.

Pectin is most commonly used as the stabiliser for acidified milk drinks. Pectin is a structural polysaccharide commonly found in the form of protopectin in plant cells. The backbone of pectin comprises α-1–4 linked galacturonic acid residues which are interrupted with a small number of 1,2 linked α-L-rhamnose units. In addition, pectin comprises highly branched regions with an almost alternating rhamno-galacturonan chain. These highly branched regions also contain other sugar units attached by glycosidic linkages to the rhamnose or galacturonic acid units. The long chains of α-1–4 linked galacturonic acid residues are commonly referred to as "smooth" regions, whereas the highly branched regions are commonly referred to as "hairy" regions.

Some of the carboxyl groups of the galacturonic residues are esterified, typically by methyl groups. The remainder are present as free carboxyl groups. Esterification of the carboxyl groups occurs after polymerisation of the galacturonic acid residues. However, it is extremely rare for all of the carboxyl groups to be esterified. Usually, the degree of esterification varies from 0 to 90% of the available carboxylic groups. If 50% or more of the carboxyl groups of a pectin are esterified, then the pectin is commonly referred to as being a high ester pectin or high methoxyl pectin. If less than 50% of the carboxyl groups are esterified, then the pectin is commonly referred to as being a low ester pectin or a low methoxyl pectin. If the pectin does not contain any, or only a few, esterified groups, it is commonly referred to as pectic acid.

The structure of the pectin, in particular the degree of esterification, dictates many of its physical and/or chemical properties. For example, pectin gelation caused by the presence of calcium cations depends especially on the degree of esterification. Gelation is believed to result from the calcium ions forming cross-linked complexes with free carboxyl groups of a number of pectin chains causing the formation of a continuous three-dimensional gelled matrix.

It is known that the distribution of the free carboxyl groups along the polymer chain is important for determining whether the pectin is suitable for use as a stabiliser for acidified milk drinks. It has been proposed that pectin stabilises a suspension of casein particles by adsorbing onto the surface of the casein particles at specific points of the pectin molecule. The remainder of the pectin molecule forms dangling chains and loops that protrude into the liquid phase. The repulsion between the resulting complexed particles may be due to the increased osmotic pressure created when pectin chains complexed to two casein particles interact with one another.

For a pectin to be useful as a stabiliser of an acidified milk drink at least some of its free carboxyl groups have to be arranged in blocks (i.e. contiguously) rather than being randomly distributed discretely along the polymer chain. The binding force between a pectin molecule and a casein particle is due to the blocks of negatively charged carboxyl groups interacting with positive charges which exist on the particle surface. The length of the blocks of free carboxyl groups is also important. Blocks of carboxyl groups that are either too long or too short do not result in stabilization of the system. In the former case, no dangling chains exist. In the latter case, the pectins do not securely attach themselves to the casein particles and therefore do not lead to stabilisation of the particles.

A well-known characteristic of low ester or calcium sensitive pectin is its ability to thicken or form gels, particularly when in the presence of alkaline earth metal cations such as $Ca^{++}$. Unfortunately, acidified milk drinks naturally contain significant quantities of calcium cations. These cations have the undesirable effect of causing significant viscosity increases if excess pectin is present which can even result, in extreme cases, in the acidified milk drink gelling.

Production of heat-treated whey drinks also presents problems. Heat treatments above 70° C. cause variable amounts of whey particles to form depending upon the precise temperature reached. The amount of pectin necessary to stabilise the heat-treated whey drink therefore varies with the heat treatment. As the whey particles that are formed are relatively small, the amount of pectin needed to obtain a stable drink can be very high due to the large total surface area of these particles. However, excessive addition of pectin will again result in thickening or gel formation due to cross-linking of the excess pectin with the naturally present calcium cations.

It will therefore be understood that the inclusion of pectin has both desirable and undesirable effects on the properties of acidified milk drinks. Whilst it can act as a stabiliser against sedimentation of casein particles or whey separation, it can have the disadvantage of increasing the viscosity of the drink due to its cross-linking with naturally co-present calcium cations rendering the drink unpalatable. It will be seen that in the absence of pectin, there is significant sedimentation in the case of both drinks caused by the instability of the casein particles which also results in relatively high viscosity. After a certain concentration of pectin has been added, the casein particles become stabilised against sedimentation after which increasing the pectin concentration has little effect on sedimentation. Turning to the viscosity of the drinks, this also significantly drops on stabilisation of the casein particles but then almost immediately begins to rise again due to cross-linking of the excess pectin added by the co-present calcium cations. This increased viscosity is undesirable as it leads to the beverage having poor organoleptic properties. This range may be as narrow as only 0.06% by weight of pectin based upon the beverage weight as a whole. Below this working range, sedimentation is a significant problem, whereas above it, the viscosity of the beverage is undesirably high.

Commercially, it is critical for manufacturers of acidified milk drinks to avoid sedimentation as this would ruin the drink. Therefore manufacturers typically add excess pectin to ensure that sedimentation does not occur but the excess pectin which is added results in the drinks having an undesirably high viscosity. Whilst manufacturers of course would like to target the narrow working range previously mentioned, this is commercially difficult due to the risk that insufficient pectin may be added causing the whole batch of drink to fail due to sedimentation.

It is well known that the methyl content of pectin is modified in nature by plant pectin esterases which are present in the plant tissue. These esterases, usually called pectin methyl esterases (PMEs), demethylate esterified carboxylic groups which are next to at least two contiguous free carboxylic acid groups. The demethylation proceeds in this way forming blocks. As previously mentioned, it is the arrangement of these blocks which is important for the stabilising action of pectin in acidified milk drinks. The proteases papain and bromelain are also known to demethylate pectins.

In a commercial, extracted pectin having a typical degree of esterification of approximately 70–74%, the length of the free carboxylic blocks may vary from molecule to molecule, and each pectin molecule typically includes several blocks of different lengths. The binding force between the pectin molecule and the surface of the casein particle depends on the length of the blocks which interact with the positive charges on the casein surface and/or with negative charges on the casein surface via calcium salt bridges. To obtain complete stability a significant proportion of the surface of a casein particle should be covered by the pectin.

As described in EP-A-0 664 300, pectins extracted from typical sources such as citrus peel can be separated or fractionated into two distinct pectin fractions. One fraction is a calcium sensitive pectin (CSP) and the other is a non-calcium sensitive pectin (NCSP). These two pectin fractions possess quite different calcium sensitivities ($\Delta$CS). CSP is a high ester pectin having a degree of esterification of at least 65% whose carboxyl groups are arranged predominantly in blocks. The block configuration of the carboxyl groups is responsible for CSP's calcium sensitivity. On the other hand, NCSP is also a high ester pectin having a degree of esterification of at least 70% whose free carboxyl groups are randomly arranged along the polymer chain with no significant degree of contiguity.

Typically commercial pectins which are marketed for use in the stabilisation of acidified milk drinks contain approximately 60% of CSP and 40% of NCSP. The pectin as a whole may have a $\Delta$CS value (as defined below) of 200 to 600 cP, whereas the CSP fraction usually has a $\Delta$CS value of 500 to 1500 cP. Since it is the CSP fraction which is responsible for stabilising casein in acidified milk drinks, the very high calcium sensitivity of this fraction is detrimental to the viscosity of the drink when the pectin, and therefore also its CSP fraction, is present in excess. In addition, since the NCSP fraction does not significantly contribute to the stabilising power of the pectin as a whole, its presence is wasted. Naturally, it would be highly desirable to have all of the pectin which is added to the acidified milk drink contribute to the stabilisation of the casein and for that pectin to have its calcium sensitivity controlled so that it does not significantly increase the viscosity of the drink when present in excess.

SUMMARY OF THE INVENTION

The present invention is directed to a modified pectin capable of stabilising a suspension of protein particles against sedimentation and which does not significantly increase the viscosity of the solution when present in significant excess compared to the amount needed to stabilise the drink against sedimentation.

The present invention relates to a pectin having:

(i) a degree of esterification (DE) of 60 to 95%, (ii) a calcium sensitivity ($\Delta$CS) of less than 25 cP, and (iii) a weight ratio of calcium sensitive pectin (CSP) to the sum of CSP and non-calcium sensitive pectin (NCSP) (hereinafter referred to as the Calcium Sensitive Pectin Ratio (CSPR)) of 0.7 or more.

The present invention also relates to a method for preparing a pectin according to the compositions set forth above, comprising the step of treating a substantially non-calcium sensitive pectin having a CSPR of 0.1 or less and a $\Delta$CS of 0–3 with a pectin deesterifying enzyme.

The present invention also relates to an aqueous acidic beverage containing a suspension of protein particles which are stabilised against sedimentation by incorporating such a pectin.

The present invention further comprehends an acidic beverage comprising at least one protein and an overdose amount of at least one blockwise, deesterified high ester pectin, said beverage composition having good organoleptic properties with the proviso that at an milk solids non fat content of 7.6%, the pectin is added in an amount greater than 0.35%.

Further, the invention also comprehends a process comprising overdosing an acidic beverage environment which contains at least one protein, with a blockwise deesterified high ester pectin, wherein a beverage is produced having good organoleptic properties with the proviso that at a milk solids non fat content of 7.6%, the pectin is added in amount greater than 0.35%.

DETAILED DESCRIPTION OF THE INVENTION

According to a first aspect, the present invention provides a pectin having:

(i) a degree of esterification (DE) of 60 to 95%, (ii) a calcium sensitivity ($\Delta$CS) of less than 25 cP, and (iii) a weight ratio of calcium sensitive pectin (CSP) to the sum of CSP and non-calcium sensitive pectin (NCSP) (hereinafter referred to as Calcium Sensitive Pectin Ratio (CSPR)) of 0.7 or more.

Preferably the DE of the pectin is 70–95%, more preferably 80–95%.

Preferably the $\Delta$CS of the pectin is less than 20, more preferably 0.5–15, most preferably in the range 2–12.

Preferably, the CSPR of the pectin is 0.85 or more, more preferably 0.9 or more.

It is preferred that the pectin has:

(i) a DE of 70 to 95%, (ii) a $\Delta$CS of less than 20, and (iii) a CSPR of 0.85 or more.

More preferably, the pectin has:

(i) a DE of 80 to 95%, (ii) a $\Delta$CS of 0.5–15, and (iii) a CSPR of 0.9 or more.

Pectins having the above characteristics have free carboxylic groups arranged in blocks of sufficient length and number so that the pectins stabilize proteins such as casein in an acidic environment such as in acidified milk drinks. However, these blocks have insufficient length and are present in insufficient numbers to cause the pectin to be overly calcium sensitive so that these pectins do not have the property of increasing the viscosity of acidified milk drinks even when added in a significant excess compared to the amount needed to stabilise the drink against sedimentation.

According to a further aspect, the present invention provides an aqueous acidic beverage containing a suspension of protein particles which are stabilised against sedimentation by a pectin of the type previously described.

According to the present invention, examples of aqueous acidified beverages are acid or acidified milk drink (such as milkshakes), yoghurt drinks, fermented milk drinks, juice milk, whey drink, drinking yoghurt, sports fortified beverage, endurance fortified beverage, fruited milk, butter milk, lactobacillus drinks, soft drinks, enteral drinks, nutritional drinks, coffee beverages, and tea beverages. The protein particles to be stabilised in these beverages may be formed from casein and/or whey.

Provided the pectin is present in an amount sufficient to stabilise the protein particles against sedimentation, then the resulting beverages have excellent stability and viscosity characteristics and have very good organoleptic properties. They have the advantage over beverages formulated with previously available pectins that the pectin can be added substantially in excess of the amount required in order to ensure stability of the protein particles against sedimentation without significantly increasing the viscosity of the beverage.

The minimum concentration of pectin needed to stabilise a beverage against deleterious sedimentation is hereafter referred to as $P_{crit}$. The value of $P_{crit}$ for a beverage/pectin system is determined from the graphical curve when the degree of sedimentation of the beverage is plotted against varying pectin concentration. $P_{crit}$ is the minimum pectin concentration required to form a stable beverage. The value of $P_{crit}$ is defined herein to be the first pectin concentration test point which is in excess of the sediment value ($S_1$) which satisfies the formula:

$$S_1=(S_{max}-S_{min})\,0.15+S_{min}$$

wherein $S_{max}$ is the maximum sediment value measured over the 0–1 % by weight pectin test range and $S_{min}$ is the minimum sediment value measured over the same test range.

$S_{max}$ is 40 and $S_{min}$ is 2. Therefore $S_1$ is 7.7. The first plotted point after $S_1$ is at a pectin concentration of 0.4% by weight, and therefore $P_{crit}$ is defined to be 0.4% by weight for this system. An amount of pectin greater than $P_{crit}$ is considered according to this invention to constitute an excess amount of pectin.

The sediment versus pectin concentration curve can readily be established for a pectin, i.e., an overdose amount of pectin and an acidified milk drink as follows.

Firstly the chemically acidified milk drink whose $P_{crit}$ is to be determined is prepared. For instance, the drink may be prepared by dissolving 1.125 kg of skimmed milk powder in 13.875 kg of water at 62° C. for 20 minutes. The resulting solution is then cooled to around 22° C. and 0.285 kg of Glucono Delta Lactone powder is added whilst stirring. The resulting solution is then left to stand without stirring at 22° C. until it reaches a pH of 4.0. The solution is then cooled to around 5° C. after which it can be stored. Before measuring the sedimentation, the acidified milk drink has however to be stirred again to ensure that no lumps remain.

The sedimentation curve is then generated by measuring sedimentation values for a succession of different added pectin concentrations. In particular, 1000 g of the acidified milk is weighed out in a beaker and then 60 g of sugar and the appropriate amount of pectin are mixed in thoroughly using a high-speed Silverson mixer. The amount of pectin added is from 0 to 10 g in 0.5 g intervals so that sedimentation is measured for a total of 21 different pectin concentrations. The solution is then left to stand for 30 minutes after which it is homogenised at 180–200 kg/cm² using a Ranni Model LAB-type 12–50 homogeniser. The resulting homogenised solution is then heated to 70° C. in a water bath with stirring, following which it is again homogenised at 180–200 kg/cm². The temperature of the resulting solution is then adjusted to 70–75° C. in a water bath with stirring and held there for ten minutes. The solution is then cooled to room temperature (for instance 20° C.) and the amount of sediment is determined by centrifugation as described below. Once the sedimentation value for all 21 different pectin concentrations has been measured, then a plot of the sediment against pectin concentration can be made.

It should be mentioned that the temperature at which acidification of the skimmed milk powder is carried out is important. If the temperature is a few degrees lower, then more pectin is required in order to obtain stability.

It is preferred that the aqueous acidic beverage provided by the present invention should include a concentration of pectin which is at least 10% by weight greater than the minimum concentration of pectin ($P_{crit}$) needed to stabilise the beverage against deleterious sedimentation. More preferably the aqueous acidic beverage includes at least 20% by weight greater, more preferably 40% by weight or more greater and even 60% by weight or more greater than $P_{crit}$.

The viscosity of the resulting aqueous acidic beverage does not exceed that of an otherwise identical beverage whose concentration of pectin is $P_{crit}$ by more than 50%, preferably 40%, more preferably 30%, more preferably 20%, and most preferably 10%.

The milk solids non-fat content of the resulting aqueous beverage may be 0.5–10% by weight, and most preferably either 0.5–3.0% by weight or 3.0–6.0% by weight.

Preferably the pH of the aqueous acidic beverage is 2.5 to less than 7, more preferably 3–6.5, and most preferably 3.5–5.5.

The pectin of the present invention can be prepared in a number of ways from a starting material such as a typical pectin mixture extracted from citrus peel, although practically any type of pectin may be subjected to processing steps leading to a pectin according to the present invention.

A mixture of naturally-occurring pectins can be represented by the following representations:

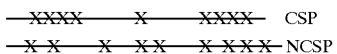

In these representations, the straight line represents the pectin backbone and each "X" represents a free carboxyl group. It will be understood that for parts of the backbone where there are no free carboxyl groups indicated, these correspond to esterified carboxyl groups. The first representation illustrates a calcium sensitive pectin as it includes blocks of contiguous carboxyl groups which are capable of binding tightly to calcium cations. On the other hand, the carboxyl groups are randomly and discretely distributed in the second representation corresponding to NCSP.

Starting with this material, the first step is to prepare a pectin which is exclusively non-calcium sensitive. One way of doing this is in accordance with the pectin fractionation technology described in EP-A-0 664 300. Such fractionation enables the separation of the NCSP fraction. The resulting separated pectin may be represented as:

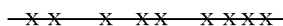

A second method of preparing the NCSP is by subjecting the starting pectin mixture to chemical and/or enzymatic pectin esterification by methods known in the art which effectively eliminates free carboxyl groups by esterifying them with lower alcohols such as methanol, ethanol, propanol or butanol, or other techniques which place amide or acetyl groups on the carboxyl groups which effectively reduces the pectin's ability to cross-link with calcium. The resulting pectin mixture may be represented as follows:

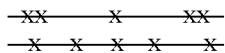

As a third alternative, the starting mixture of pectins may be treated with polygalacturonase or pectate lyase or other chemical or enzymatic techniques which selectively hydrolyze the backbone of the pectin molecule at blocks of free carboxyl groups whilst maintaining contiguous regions of methyl ester groups intact. The products resulting from such a treatment can be represented as follows:

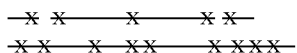

It will be understood from the above three methods that they each eliminate 10 blocks of free carboxyl groups thus preparing pectins which are substantially non-calcium sensitive. These for instance have a typical CSPR of 0.1 or less, preferably 0.01 or less, and a ΔCS of 0–3, preferably 0–1.

A skilled person may be aware of other methods for preparing the intermediate NCSP such as by extraction of specially selected raw material sources, mild extraction techniques, isolation of first extracted or "wash water" pectin or commercial sources of high ester, rapid set pectins.

The NCSP prepared as above is then subjected to a mild controlled deesterifying treatment using a pectin deesterifying enzyme such as pectin methylesterase, papain, ficin or bromelain. These enzymes deesterify a pectin to form blocks of free carboxyl groups. In more detail, a 1% aqueous solution of the NCSP is prepared using appropriate heat and agitation to ensure complete dissolution of the pectin. Then sufficient sodium chloride is added to the preparation to achieve a 1% w/v concentration of sodium chloride based on the original volume of water used in the preparation of the pectin solution. Sodium chloride is known to enhance the activity of pectin deesterifying enzymes. The temperature of this solution is then adjusted to 30–50° C. depending upon the temperature optimum of the deesterifying enzyme used. The pH of the solution is then adjusted to about 7 using 0.5 M NaOH. Then an appropriate amount of the pectin deesterifying enzyme is added to the pectin solution such as any of those produced by the methods described above in order to achieve controlled deesterification.

Particularly useful deesterifying enzymes are pectin methylesterases obtained from citrus fruit (e.g. an orange) or tomato, papain, ficin or bromelain. These are known to deesterify pectins in a block-wise manner, in the sense that it is believed they attack pectins either at non-reducing ends or next to free carboxyl groups and then proceed along the pectin molecules by a single-chain mechanism, thereby creating blocks of deesterified carboxyl groups. The present invention may also be carried out with pectin methylesterases produced by recombinant techniques. The pH of the reaction solution is maintained at about 7 by continuous addition of 0.5 M NaOH. The up-take of NaOH by the solution is used to monitor the progress of the deesterification reaction. Once the deesterification has proceeded to the required degree to produce a pectin in accordance with the invention, the reaction is terminated by the addition of acid to reduce the pH of the solution to 4 or less. The reaction mixture is then heated to around 75° C. to deactivate the enzyme followed by cooling of the mixture. The enzyme treated pectin can then be recovered from the solution by adding an equal volume of 60–80% IPA. The insoluble pectin is collected, pressed and washed with additional volumes of IPA and finally pressed to 30–50% by weight of dry matter.

The resulting deesterified pectin may be figuratively represented as follows:

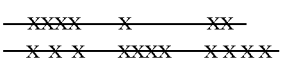

It will be seen that the resulting pectin is generally one having quite short blocks of free carboxyl groups, and importantly relatively few of such blocks. Such an arrangement of the free carboxyl groups enables the pectin to stabilise the protein particles against sedimentation, but renders the pectin substantially calcium non-sensitive so that excessive addition of such pectins to acidified milk drinks does not result in the calcium cations which are naturally present cross-linking with the pectin resulting in thickening or gel formation.

Therefore according to a further aspect of the present invention, there is provided a method for preparing a pectin as described above which comprises the step of treating a substantially non-lcium sensitive pectin having a CSPR of 0.1 or less and a ΔCS of 0–3 with a pectin deesterifying enzyme.

Preferably the substantially non-calcium sensitive pectin has a CSPR of 0.01 or less.

The pectin deesterifying enzyme is preferably a pectin methyl esterase, papain, ficin or bromelain.

ANALYTICAL PROCEDURES

In the description and in the appended Claims, pectins are characterised by their degree of esterification (DE), their calcium sensitivity (ΔCS) and their weight ratio of CSP to the sum of CSP and NCSP referred to as the calcium sensitive pectin ratio (CSPR). These three characteristics of a pectin are determinable as follows:

(i) Determination of the degree of esterification (DE) of a pectin sample.

Weigh 5 g of the pectin sample to the nearest 0.1 mg and transfer to a suitable beaker. Stir for 10 minutes with a mixture of 5 ml of fuming hydrochloric acid 37% and 100 ml of 60% IPA. Transfer to a fitted glass filter tube (30 to 60 ml capacity) and wash with six 15 ml portions of the fuming HCl-60% IPA mixture, followed by 60% IPA until the filtrate is free of chlorides. Finally wash with 20 ml of 100% IPA, dry for 2.5 hours in an oven at 105° C., cool in a desiccator and weigh. Transfer exactly one-tenth of the total net weight of the dried sample (representing 0.5 g of the original unwashed sample) to a 250 ml conical flask and moisten the sample with 2 ml of IPA. Add 100 ml of recently boiled and cooled distilled water, stopper and swirl occasionally until a complete solution is formed. Add 5 drops of phenolphthalein, titrate with 0.1 N sodium hydroxide and record the results as the initial titre ($V_1$).

Add exactly 20 ml of 0.5 N sodium hydroxide, stopper, shake vigorously and let stand for 15 minutes. Add exactly 20 ml of 0.5 N hydrochloric acid and shake until the pink colour disappears. After adding three drops of phenolphthalein, titrate with 0.1 N sodium hydroxide to a faint pink colour which persists after vigorous shaking; record this value as the saponification titre ($V_2$).

Quantitatively transfer the contents of the conical flask into a 500-ml distillation flask fitted with a Kjeldahl trap and a water-cooled condenser, the delivery tube of which extends well beneath the surface of a mixture of 150 ml of carbon dioxide-free water and 20.0 ml of 0.1 N hydrochloric acid in a receiving flask. To the distillation flask add 20 ml of a 1-in-10 sodium hydroxide solution, seal the connections, and then begin heating carefully to avoid excessive foaming. Continue heating until 80–120 ml of distillate has been collected. Add a few drops of methyl red to the receiving flask, and titrate the excess acid with 0.1 N sodium hydroxide, recording the volume required, in ml, as "S". Perform a blank determination on 20.0 ml of 0.1 N hydrochloric acid, and record the volume required, in ml, as "B". Record the amide titre (B-S) as $V_3$.

Calculate the degree of esterification (as % of total carboxyl groups) by the formula:

$$100 \times \frac{V_2}{V_1 + V_2 + V_3}$$

(ii) Determination of the calcium sensitivity ($\Delta$CS) of a pectin sample.

An aqueous solution of the pectin is prepared in distilled water and its pH adjusted to 1.5 with 1 M HCl. The concentration used should be around 0.60%. 145 g portions of this pectin solution are measured into viscosity glasses.

5 ml of a solution containing 250 mM calcium chloride is added to the 145 g pectin solution to give a final concentration of 8.3 mM calcium.

With efficient stirring with a magnetic stirrer 25 ml of an acetate buffer containing 1 M of acetate ions and a pH of 4.75 is added to the pectin solution to bring the pH to 4.2.

The magnet is taken out, and the glass is left at room temperature (25° C.) until the next day, when the viscosity is measured at 25° C. with a Brookfield viscometer.

While the method is most suitable for pectin samples having a viscosity not higher than 100, viscosity up to 200 Brookfield units can be measured with good reproducibility. Pectin samples with higher viscosity tend to gel, resulting in less reproducible results. The method, however, gives a fair indication of the relative calcium sensitivity of samples.

When the viscosity of the same pectin sample is measured without the addition of calcium chloride—diluting with distilled water instead, the $\Delta$CS value of the pectin is calculated by subtracting the measured viscosity value for the calcium free solution from the measured viscosity value for the calcium containing solution.

(iii) Determination of the CSPR of a pectin sample.

About 0.2 g of the pectin sample is weighed to the nearest mg (in a pretared 50 ml centrifuge tube weighed to the nearest mg) and is dissolved in 10 g demineralized water by heating the tube to 70° C. The solution is cooled to approximately 20° C. This is done in duplicate. The pH of each solution is adjusted to 4.0.

The total amount of pectin in the solution is determined by adding 20 ml of 80% isopropyl alcohol (IPA) to one of the tubes to precipitate the pectin. The precipitate is collected by centrifugation at 30,000 G for 30 minutes, washed twice with 60% IPA following up each wash with centrifugation, dried at 60° C. overnight under vacuum and weighed to the nearest mg. The amount of pectin precipitated is divided by the initial weight of pectin added to that particular tube to yield a ratio "A" for the pectin.

10 ml of the following solution (which contains 60 mM calcium and 16 percent IPA) is added to the remaining 10 ml sample of pectin solution in a tared centrifuge tube:

387 g demineralized water
99 g 80% IPA
4.4 g $CaCl_2$, 2 $H_2O$.

After mixing of the two solutions, this results in a Ca-content of 30 mM and 8% IPA. The suspension of gel particles formed is left for 24 hours with occasional stirring. The gel particles are separated from the liquid phase by centrifugation at 30,000 G for 30 minutes. The liquid phase is carefully decanted or siphoned off to leave the gel particles in the tube.

The gel particles are washed twice in equal amounts of a solution containing 30 mM Ca and 8% IPA by vortexing and allowing the wash to equilibrate. The equilibration time is 24 hours for each washing. Following each wash the gel particles are separated using centrifugation at 30,000 G for 30 minutes. The washing solution for this step can be prepared by diluting an aliquot of the 16% IPA–60 mM calcium solution with an equal volume of water.

The total amount of washed gel phase is then weighed after decanting off the liquid phase. The amount of pectin in the gel phase is determined by mixing the gel phase, weighed out to the second decimal, with twice its value of 80% IPA and then washed twice in 60% IPA. The precipitate is collected by centrifugation at 30,000 G for 30 minutes after each wash. The sample is then dried at 60° C. overnight under vacuum and weighed to the nearest mg. The normalized amount of CSP pectin is determined by dividing this amount of pectin by the original amount of pectin weighed into the centrifuge tube. This is designated the "B" value for the pectin.

The CSPR is calculated according to the formula CSPR=B/A.

(iv) Determination of sediment and viscosity

In the description which follows, reference is also made to the determination of the amount of sediment in an acidified milk drink and the determination of the viscosity of such a drink. In order to determine the amount of sediment, accurately weighed centrifuge tubes are filled with the acidified milk drink to within 1 centimeter of their rim. The tubes are again weighed which provides the weight of the sample of drink in the tube. The tube is then centrifuged for 20 minutes at 4,500 rpm. The supernatant is then decanted and the tubes placed upside-down for 30 minutes to drain away any remaining liquid. Finally, the rim of the tube is wiped with a tissue and the tube finally weighed. The sediment (expressed as a percentage) is calculated by dividing the weight of sediment by the weight of the originally taken sample and expressing the result as a percentage.

The viscosity of an acidified milk drink is measured by filling a viscosity glass with the drink and leaving this for 18–24 hours at 5° C. The viscosity is then measured with a Brookfield Viscosimeter type LVT at 60 rpm after rotating for 1 minute.

EXAMPLES

The present invention will now be described in more detail by way of the following Examples. These should be understood as being illustrative of the invention but not limiting thereof.

Example 1

Preparation of a Pectin According to the Present Invention 12.5 g of milled, dry high methoxyl pectin Hercules GENU® pectin type JM was dispersed in a litre of solution containing 250 ml of 80% IPA, 750 ml of distilled water and 4.4 g of $CaCl_2$; 2 $H_2O$. This dispersion was stirred gently and its pH was adjusted to around 3.8 with sodium carbonate. The reaction mass was separated using a nylon cloth to isolate the desired NCSP fraction. The starting material had a DE of 70%, a ΔCS of 470 and a CSPR of 0.5. The NCSP fraction which was isolated had a DE of 77%, a ΔCS of 0 and a CSPR of 0.

The resulting isolated NCSP fraction was then used to prepare a 1% aqueous solution by heating to 75° C. together with agitation. Sufficient sodium chloride was then added to achieve a 1% w/v concentration. The temperature of the solution was then adjusted to 40° C. and its pH adjusted to 7.0 using NaOH. Then 1 g of papain obtained from Enzyme Devlopment Corporation, New York, N.Y. was added to the pectin solution to mildly deesterify the pectin. The pH of the reaction solution was maintained at 7.0 by continuous addition of 0.5 M NaOH and this addition was used to monitor the progress of the deesterification reaction. After 1 hour the reaction was terminated by the addition of hydrochloric acid to reduce the pH to around 4.0. The reaction mixture was then heated to 80° C. to deactivate the papain after which the reaction mixture was cooled to 40° C. Finally, the resulting pectin was recovered from the solution by addition of an equal volume of 70% by weight IPA. The resulting insoluble pectin was collected, pressed and washed with additional volumes of IPA. The resulting pectin was found to have a DE of 72%, a ΔCS of 5 and a CSPR of 0.95.

Example 2

Preparation of 8.5% By Weight MSNF Acidified Milk Drinks

The pectin prepared in Example 1 and a typical prior art juice milk pectin Hercules GENU® pectin type JM were separately used to prepare 8.5% by weight milk solids non-fat (MSNF) homogenised and heat treated yoghurt drinks. The sedimentation and viscosity curves for such drinks with varying pectin concentrations were then prepared as described above. Whilst both the juice milk pectin and the pectin of Example 1 have a good stabilising effect against sedimentation when present in an amount of above about 0.25 weight %, the juice milk pectin undesirably causes the viscosity of the drinking yoghurt to rise when it is present in an amount of 0.3% by weight or greater. In contrast, the pectin produced in Example 1 resulted in either no or minimal increase in the viscosity of the drinking yoghurt when present in excess. This results in a significant improvement in the working concentration range of the pectin of the present invention making it possible to use this pectin at levels significantly in excess of $P_{crit}$ (0.25 weight %) which ensures sufficiently low sedimentation levels without the detrimental effect of increasing viscosity of the drinking yoghurt.

Example 3

Preparation of 1.1% By Weight MSNF Acidified Milk Drinks

In a similar way to Example 2, the commercially available juice milk pectin used in Example 2 and the pectin produced in Example 1 were separately used to prepare 1.1% by weight MSNF acidified milk drinks which were homogenised and heat treated. Again, it will be seen that the commercially available pectin causes a significant increase in viscosity of the acidified milk drink when used in concentrations of $P_{crit}$ (0.2% by weight) or above. In contrast, the pectin of Example 1 does not lead to any increased viscosity of the acidified milk drink even when used in concentrations which are double that of $P_{crit}$.

Example 4

Preparation of 3.0% By Weight MSNF Acidified Milk Drinks

In a similar way to Example 2, the commercially available juice milk pectin used in Example 2 and the pectin produced in Example 1 were separately used to prepare 3.0% by weight MSNF acidified milk drinks which were homogenised and heat treated. Again, it will be seen that the commercially available pectin causes a significant increase in viscosity of the acidified milk drink when used in concentrations of $P_{crit}$ (0.15% by weight) or above. In contrast, the pectin of Example 1 does not lead to any increased viscosity of the acidified milk drink even when used in concentrations which are double that of $P_{crit}$.

What is claimed is:

1. A pectin preparation having:
   (i) a degree of esterification (DE) of 60 to 95%,
   (ii) a calcium sensitivity (ΔCS) of less than 25 cP, and
   (iii) a calcium sensitive pectin weight ratio (CSPR) of calcium sensitive pectin (CSP) to the sum of CSP and non-calcium sensitive pectin (NCSP) of 0.7 or more.

2. The pectin preparation according to claim 1, having:
   (i) a DE of 70 to 95%,
   (ii) a ΔCS of less than 20 cP, and
   (iii) a CSPR of 0.85 or more.

3. The pectin preparation according to claim 2, having:
   (i) a DE of 80 to 95%,
   (ii) a ΔCS of 0.5–15 cP, and
   (iii) a CSPR of 0.9 or more.

4. The pectin preparation according to claim 3, having a ΔCS of 2–12 cP.

5. A method for preparing a pectin preparation according to any of claims 1 to 4, comprising treating a non-calcium sensitive pectin having a CSPR of 0.1 or less and a ΔCS of 0–3 cP with a pectin deesterifying enzyme.

6. The method according to claim 5, wherein the non-calcium sensitive pectin has a CSPR of 0.01 or less.

7. The method according to claim 5, wherein the pectin deesterifying enzyme is a pectin, methylesterase, papain, ficin or bromelain.

8. An aqueous acidic beverage comprising a suspension of protein particles which are stabilized against sedimentation by a pectin preparation according to claim 1.

9. The aqueous acidic beverage according to claim 8, wherein the protein particles comprise casein.

10. The aqueous acidic beverage according to claim 8, wherein the concentration of pectin is at least 10% by weight greater than the minimum concentration of pectin $P_{crit}$.

11. The aqueous acidic beverage according to claim 10, having a viscosity which is no more than 50% higher than a comparative aqueous acidic beverage, said comparative aqueous acidic beverage, with the exception of pectin content, being identical to the aqueous acidic beverage, said comparative aqueous acidic beverage having a pectin concentration $P_{crit}$ and said aqueous acidic beverage having a concentration greater than $P_{crit}$.

12. The aqueous acidic beverage according to claim 8, wherein the beverage has a milk solids non-fat content of 0.5 to 10% by wt.

13. The aqueous acidic beverage according to claim 8, wherein the pH is 2.5 to less than 7.

14. The aqueous acidic beverage according to claim 8, wherein the beverage is a drinking yoghurt.

15. An acidic beverage comprising at least one protein and an overdose amount of at least one blockwise, deesterified high ester pectin preparation, said pection preparation having
 (i) a degree of esterification (DE) of 60 to 95%,
 (ii) a calcium sensitivity (ΔCS) of less than 25 cP, and
 (iii) a calcium sensitive pectin weight ratio (CSPR) of calcium sensitive pectin (CSP) to the sum of CSP and non-calcium sensitive pectin (NCSP) of 0.7 or more.

16. The aqueous acidic beverage of claim 8, wherein the beverage is selected from the group consisting of acid or acidified milk drink, yogurt drinks, fermented milk drinks, juice milk, whey drink, drinking yogurt, sports fortified beverage, endurance fortified beverage, fruited milk, butter milk, lactobacllius drinks, soft drinks, enteral drinks, nutritional drinks, coffee beverages, and tea beverages.

17. The acidic beverage of claim 15, wherein the acidic beverage comprises an aqueous solution.

18. The aqueous acidic beverage of claim 8, having a pH of at least 2.5.

19. The aqueous acidic beverage of claim 8, having a pH of at least 3.0.

20. The aqueous acidic beverage of claim 8, having a pH of at least 3.5.

21. The aqueous acidic beverage of claim 8, having an upper pH limit of less than 7.

22. The aqueous acidic beverage of claim 8, having an upper pH limit of less than or equal to 6.5.

23. The aqueous acidic beverage of claim 8, having an upper pH limit of less than or equal to 5.5.

24. The aqueous acidic beverage of claim 8, wherein the beverage is an acidified milk drink.

25. The aqueous acidic beverage of claim 8, wherein the beverage is a yoghurt drink.

26. The aqueous acidic beverage of claim 8, wherein the beverage has a milk solids non-fat content of greater than or equal to 0.5% by weight.

27. The aqueous acidic beverage of claim 8, wherein the beverage has a milk solids non-fat content of greater than or equal to 1.0% by weight.

28. The aqueous acidic beverage of claim 8, wherein the beverage has a milk solids non-fat content of greater than or equal to 3.0% by weight.

29. The aqueous acidic beverage of claim 8, wherein the beverage has a milk solids non-fat content of less than or equal to 10.0% by weight.

30. The aqueous acidic beverage of claim 8, wherein the beverage has a milk solids non-fat content of less than or equal to 8.0% by weight.

31. The aqueous acidic beverage of claim 8, wherein the beverage has a milk solids non-fat content of less than or equal to 60% by weight.

32. The aqueous acidic beverage of claim 8, wherein the pectin preparation is added in an amount that is at least 10% greater than $P_{crit}$.

33. The aqueous acidic beverage of claim 8, wherein the pectin preparation is added in an amount that is at least 20% greater than $P_{crit}$.

34. The aqueous acidic beverage of claim 8, wherein the pectin preparation is added in an amount that is at least 40% greater than $P_{crit}$.

35. The aqueous acidic beverage of claim 8, wherein the pectin preparation is added in an amount that is at least 60% greater than $P_{crit}$.

36. The aqueous acidic beverage of claim 8, wherein the beverage has a milk solids non-fat content of from about 0.5 to about 3.0% by weight.

37. The aqueous acidic beverage of claim 36, wherein the pectin preparation is added in an amount that is at least 10% greater than $P_{crit}$.

38. The aqueous acidic beverage of claim 36, wherein the pectin preparation is added in an amount that is at least 20% greater than $P_{crit}$.

39. The aqueous acidic beverage of claim 36, wherein the pectin preparation is added in an amount that is at least 40% greater than $P_{crit}$.

40. The aqueous acidic beverage of claim 36 wherein the pectin preparation is added in an amount that is at least 60% greater than $P_{crit}$.

41. The aqueous acidic beverage of claim 36, having a change of viscosity which is less than 50% as compared to a viscosity at $(P_{crit})$.

42. The aqueous acidic beverage of claim 36, having a change of viscosity which is less than 40% as compared to a viscosity at $(P_{crit})$.

43. The aqueous acidic beverage of claim 36, having a change of viscosity which is less than 30% as compared to the viscosity at $(P_{crit})$.

44. The aqueous acidic beverage of claim 36, having a change of viscosity which is less than 20% as compared to the viscosity at $(P_{crit})$.

45. The aqueous acidic beverage of claim 36, having a change of viscosity which is less than 10% as compared to the viscosity at $(P_{crit})$.

46. The aqueous acidic beverage of claim 8, wherein the beverage has a milk solids non-fat content of from about 3.0 to about 6.0% by weight.

47. The aqueous acidic beverage of claim 46, wherein the pectin preparation is added in an amount that is at least 10% greater than $P_{crit}$.

48. The aqueous acidic beverage of claim 46, wherein the pectin preparation is added in an amount that is at least 20% greater than $P_{crit}$.

49. The aqueous acidic beverage of claim 46, wherein the pectin preparation is added in an amount that is at least 40% greater than $P_{crit}$.

50. The aqueous acidic beverage of claim 46 wherein the pectin preparation is added in an amount that is at least 60% greater than $P_{crit}$.

51. The aqueous acidic beverage of claim 46, having a change of viscosity which is less than 50% as compared to a viscosity at $(P_{crit})$.

52. The aqueous acidic beverage of claim 46, having a change of viscosity which is less than 40% as compared to a viscosity at $(P_{crit})$.

53. The aqueous acidic beverage of claim 46, having a change of viscosity which is less than 30% as compared to the viscosity at $(P_{crit})$.

54. The aqueous acidic beverage of claim 46, having a change of viscosity which is less than 20% as compared to the viscosity at ($P_{crit}$).

55. The aqueous acidic beverage of claim 46, having a change of viscosity which is less than 10% as compared to the viscosity at ($P_{crit}$).

56. The aqueous acidic beverage of claim 8, wherein the beverage has a milk solids non-fat content of greater than 6% by weight.

57. The aqueous acidic beverage of claim 56, wherein the pectin preparation is added in an amount that is at least 10% greater than $P_{crit}$.

58. The aqueous acidic beverage of claim 56, wherein the pectin preparation is added in amount that is at least 20% greater than $P_{crit}$.

59. The aqueous acidic beverage of claim 56, wherein the pectin preparation is added in an amount that is at least 40% greater than $P_{crit}$.

60. The aqueous acidic beverage of claim 56 wherein the pectin preparation is added in an amount that is at least 60% greater than $P_{crit}$.

61. The aqueous acidic beverage of claim 56, having a change of viscosity which is less than 50% as compared to a viscosity at ($P_{crit}$).

62. The aqueous acidic beverage of claim 56, having a change of viscosity which is less than 40% as compared to a viscosity at ($P_{crit}$).

63. The aqueous acidic beverage of claim 56, having a change of viscosity which is less than 30% as compared to the viscosity at ($P_{crit}$).

64. The aqueous acidic beverage of claim 56, having a change of viscosity which is less than 20% as compared to the viscosity at ($P_{crit}$).

65. The aqueous acidic beverage of claim 56, having a change of viscosity which is less than 10% as compared to the viscosity at ($P_{crit}$).

66. The aqueous acidic beverage of claim 8, wherein the protein is casein or whey protein.

67. The aqueous acidic beverage of claim 8, wherein the degree of esterification of the pectin preparation is at least 70%.

68. The aqueous acidic beverage of claim 8, wherein the degree of esterification of the pectin preparation is at least 80%.

69. The aqueous acidic beverage of claim 8, wherein the calcium sensitivity of the pectin preparation is less than 15 cP.

70. The aqueous acidic beverage of claim 8, wherein the calcium sensitivity of the pectin preparation is less than 10 cP.

71. The aqueous acidic beverage of claim 8, wherein the calcium sensitivity of the pectin preparation is less than 5 cP.

72. The aqueous acidic beverage of claim 8, wherein the calcium sensitivity of the pectin preparation is 1 cP.

73. The aqueous acidic beverage of claim 8, wherein the pectin preparation has a CSPR of greater than 0.7.

74. The aqueous acidic beverage of claim 8, wherein the pectin preparation has a a CSPR of greater than 0.85.

75. The aqueous acidic beverage of claim 8, wherein the pectin preparation has a a CSPR of greater than 0.9.

76. The aqueous acidic beverage of claim 8, having a change of viscosity which is less than 50% as compared to a viscosity at ($P_{crit}$).

77. The aqueous acidic beverage of claim 8, having a change of viscosity which is less than 40% as compared to a viscosity at ($P_{crit}$).

78. The aqueous acidic beverage of claim 8, having a change of viscosity which is less than 30% as compared to a viscosity at ($P_{crit}$).

79. The aqueous acidic beverage of claim 8, having a change of viscosity which is less than 20% as compared to a viscosity at ($P_{crit}$).

80. The aqueous acidic beverage of claim 8, having a change of viscosity which is less than 10% as compared to a viscosity at ($P_{crit}$).

81. A process comprising overdosing an acidic beverage which contains at least one protein, with a blockwise deesterified high ester pectin preparation, said pectin preparation having
(i) a degree of esterification (DE) of 60 of 95%,
(ii) a calcium sensitivity (ΔCS) of less than 25 cP, and
(iii) a calcium sensitive pectin weight ratio (CSPR) of calcium sensitive pectin (CSP) to the sum of CSP and non-calcium sensitive pectin (NCSP) of 0.7 or more.

82. The process of claim 81, wherein the beverage is selected from the group consisting of acid or acidified milk drink, yogurt drinks, fermented milk drinks, juic milk, whey drink, drinking yogurt, sports fortified beverage, endurance fortified beverage, fruited milk, butter milk, lactobacillus drinks, soft drinks, enteral drinks, nutritional drinks, coffee beverages, and tea beverages.

83. The process of claim 81, wherein the acidic beverage comprises an aqueous solution.

84. The process of claim 81, wherein the the acidic beverage has a pH of at least 2.5.

85. The process of claim 81, wherein the the acidic beverage has a pH of at least 3.0.

86. The process of claim 81, wherein the the acidic beverage has a pH of at least 3.5.

87. The process of claim 81, wherein the acidic beverage has an upper pH limit of less than 7.

88. The process of claim 81, wherein the acidic beverage has an upper pH limit of less than 6.5.

89. The process of claim 81, wherein the acidic beverage has an upper pH limit of less than 5.5.

90. The process of claim 81, wherein the beverage is an acidified milk drink.

91. The process of claim 81, wherein the beverage is a yoghurt drink.

92. The process of claim 81, wherein the beverage has a milk solids non-fat content of greater than or equal to 0.5% by weight.

93. The process of claim 81, wherein the beverage has a milk solids non-fat content of greater than or equal to 1.0% by weight.

94. The process of claim 81, wherein the beverage has a milk solids non-fat content of greater than ord equal to 3.0% by weight.

95. The process of claim 81, wherein the beverage has a milk solids non-fat content of less than or equal to 10.0% by weight.

96. The process of claim 81, wherein the beverage ha s milk solids non-fat content of less than or equal to 8.0% by weight.

97. The process of claim 81, wherein the beverage has milk solids non-fat content of less than or equal to 6.0% by weight.

98. The process of claim 81, wherein the pectin preparation is added in an amount that is at least 10% greater than $P_{crit}$.

99. The process of claim 81, wherein the pectin preparation is added in an amount that is at least 20% greater than $P_{crit}$.

100. The process of claim 81, wherein the pectin preparation is added in an amount that is at least 40% greater than $P_{crit}$.

101. The process of claim 81, wherein the pectin preparation is added in an amount that is at least 60% greater than $P_{crit}$.

102. The process of claim 81, wherein the milk solids non-fat content is from about 0.5 to about 3.0% by weight.

103. The process of claim 102, wherein the pectin preparation is added in an amount that is at least 10% greater than $P_{crit}$.

104. The process of claim 102, wherein the pectin preparation is added in an amount that is at least 20% greater than $P_{crit}$.

105. The process of claim 102, wherein the pectin preparation is added in an amount that is at least 40% greater than $P_{crit}$.

106. The process of claim 102, wherein the pectin preparation is added in an amount that is at least 60% greater than $P_{crit}$.

107. The process of claim 102, wherein the beverage has a change of viscosity which is less than 50% as compared to a viscosity at $(P_{crit})$.

108. The process of claim 102, wherein the beverage has a change of viscosity which is less than 40% as compared to a viscosity at $(P_{crit})$.

109. The process of claim 102, wherein the beverage has a change of viscosity which is less than 30% as compared to a viscosity at $(P_{crit})$.

110. The process of claim 102, wherein the beverage has a change of viscosity which is less than 20% as compared to a viscosity at $(P_{crit})$.

111. The process of claim 102, wherein the beverage has a change of viscosity which is less than 10% as compared to a viscosity at $(P_{crit})$.

112. The process of claim 81, wherein the milok solids non-fat content is from about 3.0 to about 6.0% by weight.

113. The process of claim 112, wherein the pectin preparation is added in an amount that is at least 10% greater than $P_{crit}$.

114. The process of claim 112, wherein the pectin preparation is added in an amount that is at least 20% greater than $P_{crit}$.

115. The process of claim 112, wherein the pectin preparation is added in an amount that is at least 40% greater than $P_{crit}$.

116. The process of claim 112, wherein the pectin preparation is added in an amount that is at least 60% greater than $P_{crit}$.

117. The process of claim 112, where the beverage has a change of viscosity which is less than 50% as compared to a viscosity at $(P_{crit})$.

118. The process of claim 112, wherein the beverage has a change of viscosity which is less than 40% as compared to a viscosity at $(P_{crit})$.

119. The process of claim 112, wherein the beverage has a change of viscosity which is less than 30% as compared to a viscosity at $(P_{crit})$.

120. The process of claim 112, wherein the beverage has a change of viscosity which is less than 20% as compared to a viscosity at $(P_{crit})$.

121. The process of claim 112, wherein the beverage has a change of viscosity which is less than 10% as compared to a viscosity at $(P_{crit})$.

122. the process of claim 81, wherein the milk solids non-fat content is greater than 6% by weight.

123. The process of claim 122, wherein the pectin preparation is added in an amount that is at least 10% greater than $P_{crit}$.

124. The process of claim 122, wherein the pectin preparation is added in an amount that is at least 20% greater than $P_{crit}$.

125. The process of claim 122, wherein the pectin preparation is added in an amount that is at least 40% greater than $P_{crit}$.

126. The process of claim 122, wherein the pectin preparation is added in an amount that is at least 60% greater than $P_{crit}$.

127. The process of claim 122, wherein the beverage has a change of viscosity which is less than 50% as compared to a viscosity at $(P_{crit})$.

128. The process of claim 122, wherein the beverage has a change of viscosity which is less than 40% as compared to a viscosity at $(P_{crit})$.

129. The process of claim 122, wherein the beverage has a change of viscosity which is less than 30% as compared to a viscosity at $(P_{crit})$.

130. The process of claim 122, wherein the beverage has a change of viscosity which is less than 20% as compared to a viscosity at $(P_{crit})$.

131. The process of claim 122, wherein the beverage has a change of viscosity which is less than 10% as compared to a viscosity at $(P_{crit})$.

132. The process of claim 81, wherein the protein is casein or whey protein.

133. The process of claim 81, wherein the degree of esterification of the high ester pectin preparation is at least 70%.

134. The process of claim 81, wherein the degree of esterification of the high ester pectin preparation is at least 80%.

135. The process of claim 81, wherein the calcium sensitivity value of the high ester pectin preparation is less than 15 cP.

136. The process of claim 81, wherein the calcium sensitivity value of the high ester pectin preparation is less than 10cP.

137. The process of claim 81, wherein the calcium sensitivity value of the high ester pectin preparation is less than 5 cP.

138. The procses of claim 81, wherein the calcium sensitivity value of the high ester pectin preparation is 1 cP.

139. The process of claim 81, wherein the high ester pectin preparation has a CSPR greater than 0.7.

140. The process of claim 81, wherein the high ester pectin preparation has a CSPR greater than 0.85.

141. The process of claim 81, wherein the high ester pectin preparation has a CSPR greater than 0.9.

142. The process of claim 81, wherein the beverage has a change of viscosity which is less than 50% as compared to a viscosity at $(P_{crit})$.

143. The process of claim 81, wherein the beverage has a change of viscosity which is less than 40% as compared to a viscosity at $(P_{crit})$.

144. The process of claim 81, wherein the beverage has a change of viscosity which is less than 30% as compared to a viscosity at $(P_{crit})$.

145. The process of claim 81, wherein the beverage has a change of viscosity which is less than 20% as compared to a viscosity at $(P_{crit})$.

146. The process of claim 81, wherein the beverage has a change of viscosity which is less than 10% as compared to a viscosity at $(P_{crit})$.

* * * * *